(12) United States Patent
Chen et al.

(10) Patent No.: US 11,197,770 B2
(45) Date of Patent: Dec. 14, 2021

(54) BIFURCATED FLOW DIVERTER SYSTEMS

(71) Applicant: Baylor College of Medicine, Houston, TX (US)

(72) Inventors: Stephen P. Chen, Houston, TX (US); Peter Tze Man Kan, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 292 days.

(21) Appl. No.: 16/604,786

(22) PCT Filed: May 7, 2018

(86) PCT No.: PCT/US2018/031371
§ 371 (c)(1),
(2) Date: Oct. 11, 2019

(87) PCT Pub. No.: WO2018/208662
PCT Pub. Date: Nov. 15, 2018

(65) Prior Publication Data
US 2021/0282944 A1 Sep. 16, 2021

Related U.S. Application Data

(60) Provisional application No. 62/502,945, filed on May 8, 2017.

(51) Int. Cl.
*A61F 2/852* (2013.01)
*A61F 2/954* (2013.01)
(Continued)

(52) U.S. Cl.
CPC .............. *A61F 2/852* (2013.01); *A61F 2/856* (2013.01); *A61F 2/954* (2013.01); *A61F 2/958* (2013.01);
(Continued)

(58) Field of Classification Search
CPC .. A61F 2/82; A61F 2/852; A61F 2/856; A61F 2/954; A61F 2/958; A61F 2/962;
(Continued)

(56) References Cited

U.S. PATENT DOCUMENTS 4,762,129 A 8/1988 Bonzel
5,061,273 A 10/1991 Yock
(Continued)

FOREIGN PATENT DOCUMENTS

WO 9915103 A1 4/1999

OTHER PUBLICATIONS

CardioVascular Technologies, Inc., "Rapid Exchange (RX) Catheter Platform Technology Overview", 2010, 40 pages.
(Continued)

*Primary Examiner* — George J Ulsh
(74) *Attorney, Agent, or Firm* — Saul Ewing Arnstein & Lehr LLP; Kathryn Doyle; Brian R. Landry

(57) ABSTRACT

One aspect of the invention provides a flow-diverting system including: a first stent having a proximal end, a distal end and a first sidewall opening; and a second stent having a proximal end, a distal end and a second sidewall opening. The first sidewall opening is of sufficient size for the distal end of the second stent to pass from inside the first stent through the first sidewall opening. The second sidewall opening is of sufficient size for fluid flow from inside the second stent through the second sidewall opening into the first stent.

16 Claims, 9 Drawing Sheets

(51) Int. Cl.
*A61F 2/856* (2013.01)
*A61F 2/958* (2013.01)
*A61F 2/82* (2013.01)

(52) U.S. Cl.
CPC ... *A61F 2002/826* (2013.01); *A61F 2230/006* (2013.01); *A61F 2230/0052* (2013.01)

(58) Field of Classification Search
CPC ............... A61F 2/966; A61F 2002/826; A61F 2230/0052; A61F 2230/006
See application file for complete search history.

(56) References Cited

U.S. PATENT DOCUMENTS

| | | | |
|---|---|---|---|
| 5,738,667 | A | 4/1998 | Solar |
| 5,891,191 | A | 4/1999 | Stinson |
| 6,409,750 | B1 | 6/2002 | Hyodoh et al. |
| 6,520,983 | B1 | 2/2003 | Colgan et al. |
| 8,529,618 | B2 | 9/2013 | Davis et al. |
| 9,149,373 | B2 | 10/2015 | Davis et al. |
| 2002/0077692 | A1 | 6/2002 | Besselink |
| 2004/0220653 | A1 | 11/2004 | Borg et al. |
| 2006/0052858 | A1 | 3/2006 | Wilson et al. |
| 2008/0221600 | A1 | 9/2008 | Dieck et al. |
| 2009/0043373 | A1 | 2/2009 | Arnault De La Menardiere et al. |
| 2012/0046731 | A1 | 2/2012 | Von et al. |
| 2012/0197378 | A1 | 8/2012 | Houser |
| 2013/0245745 | A1 | 9/2013 | Vong et al. |
| 2013/0282106 | A1 | 10/2013 | Davis et al. |
| 2015/0119972 | A1 | 4/2015 | Davis et al. |
| 2016/0038153 | A1 | 2/2016 | Losordo et al. |
| 2016/0100966 | A1 | 4/2016 | Bourang |
| 2016/0199204 | A1 | 7/2016 | Pung et al. |
| 2016/0302797 | A1 | 10/2016 | Cam et al. |
| 2016/0310077 | A1 | 10/2016 | Hunter et al. |
| 2016/0361180 | A1 | 12/2016 | Vong et al. |

OTHER PUBLICATIONS

International Search Report and Written Opinion, International Patent Application No. PCT/US2018/031371, dated Jul. 30, 2018.
MicroVention, "FRED Flow Re-Direction Endoluminol Device, Integrated Dual-Layer System for Optimal Performance and Ease of Use", MicroVention, Inc., 2018.
Society of Neuro Interventional Surgery, "Treatment of Brain Aneurysms by Endovascular Coiling", http://www.brainaneurysm.com/treatment, printed Apr. 24, 2017, 2 pages.
Albert, J. G., et al., "Over-the-Wire Stent Exchange Using a Simple Snare Technique in Endoscopic Retrograde Cholangiopancreatography", Video Journal & Encyclopedia GI Endoscopy, 2013.
Kern, M. J., "ACIST Rxi: A Monorail pressure microcatheter", University of California, Irvine, U.S. Department of Veterans Affairs, 22 pages.
Mohlenbruch, M. A., et al., "The FRED Flow-Diverter Stent for Intracranial Aneurysms: Clinical Study to Assess Safety and Efficacy", Am J Neuroradiol, 2015, 7 pages.
Moussa, I. D., "Technical Variations of Two-Stent Bifurcation Treatment", Weill Medical College of Cornell University, New York, downloaded Mar. 24, 2017, 68 pages.

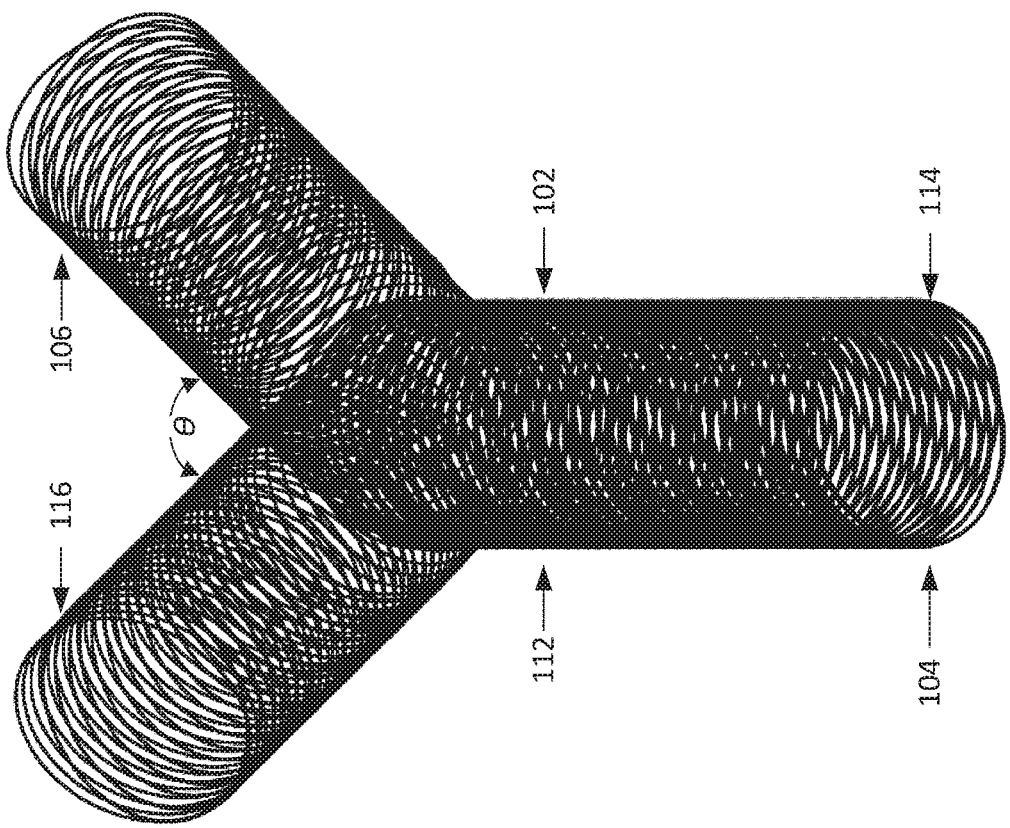
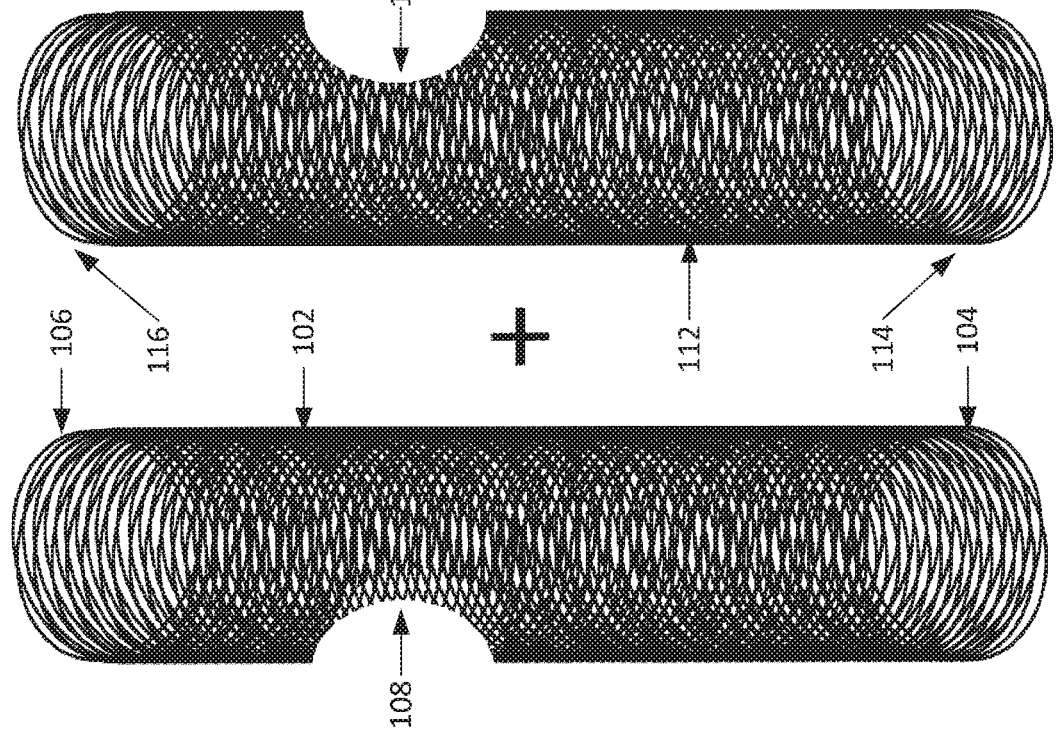
FIG. 1

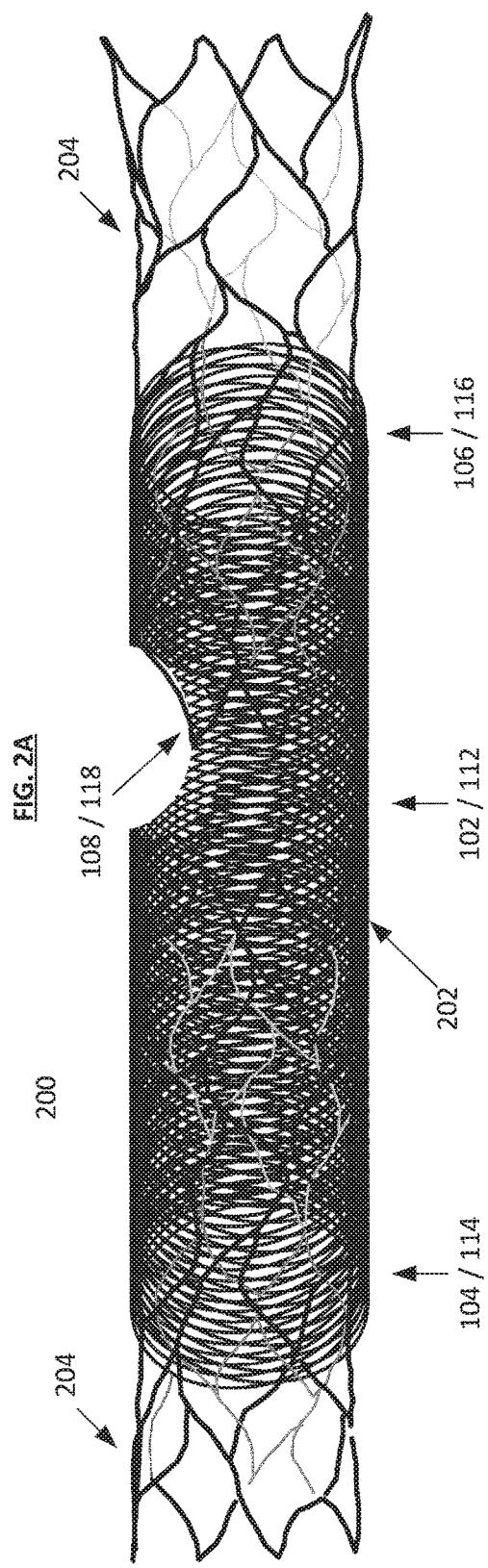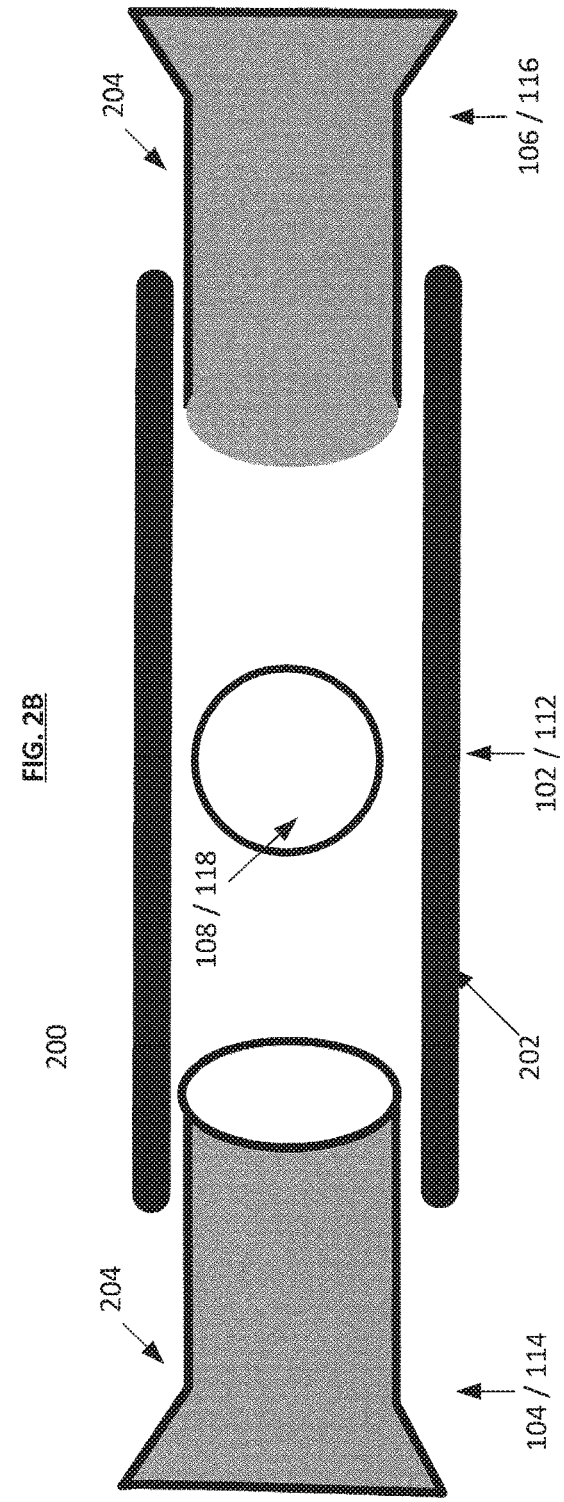

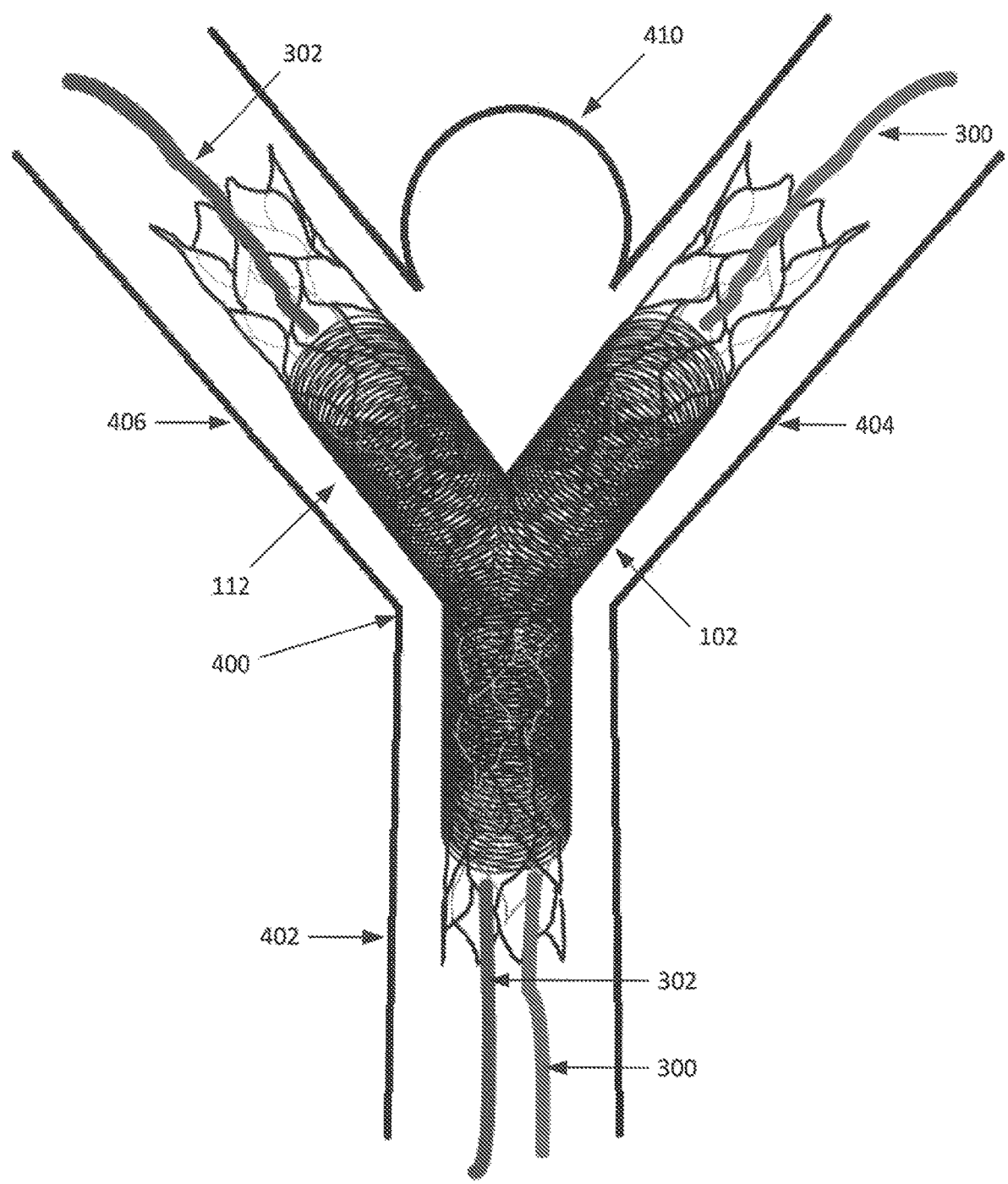

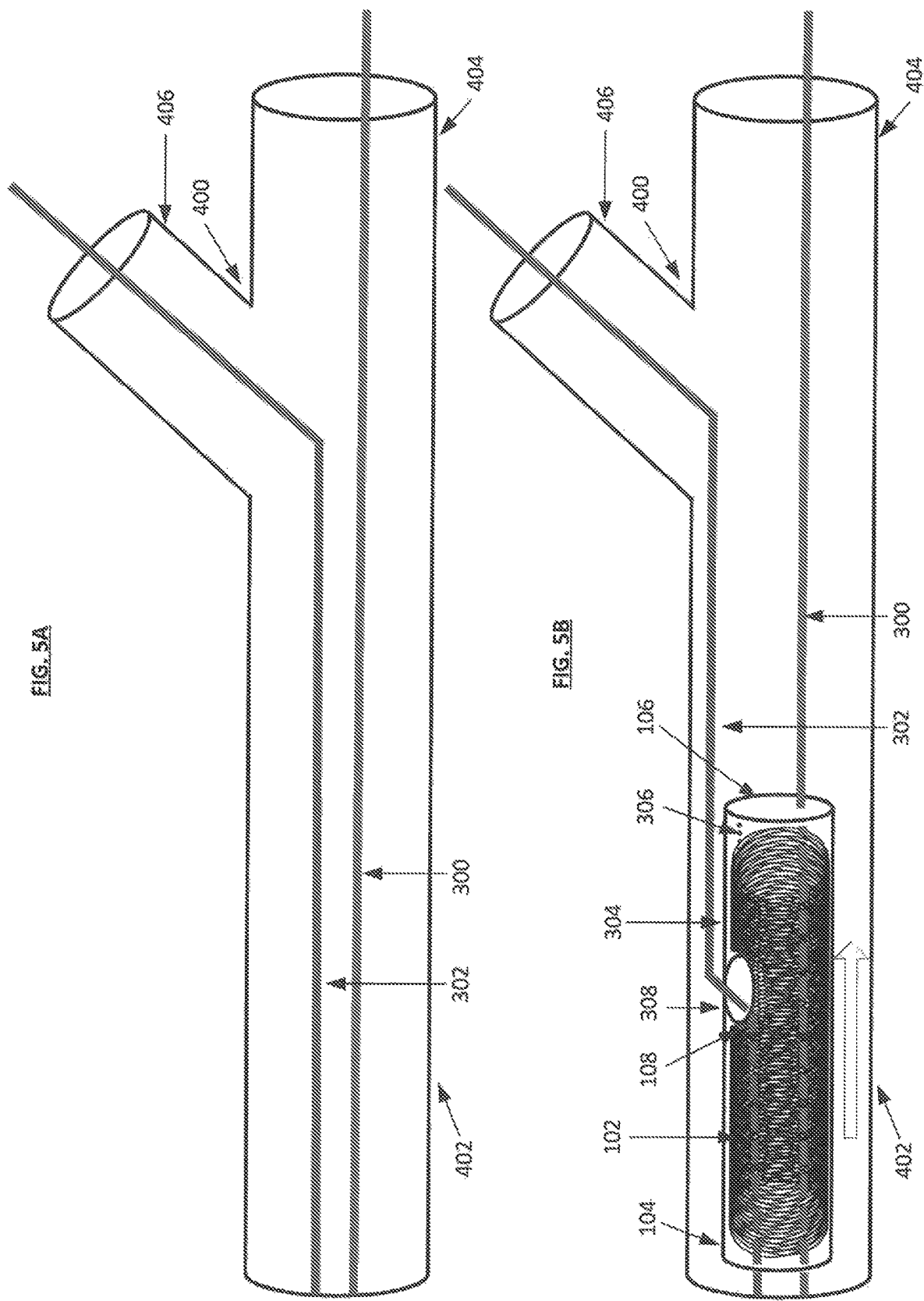

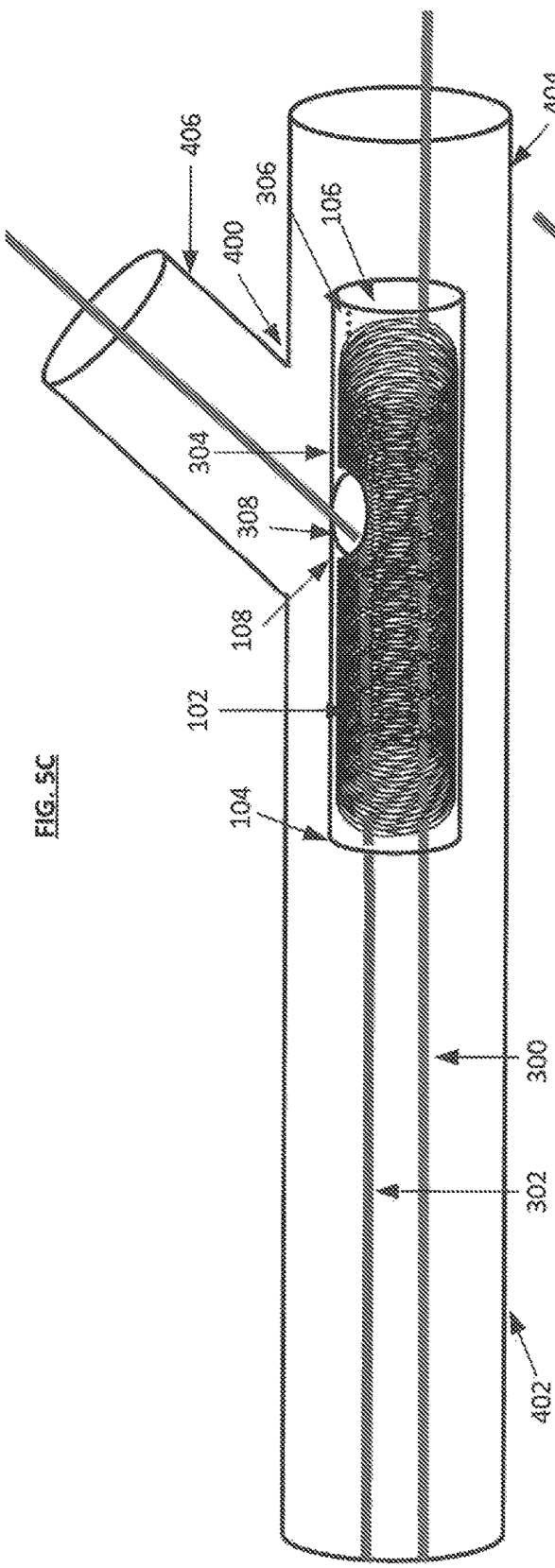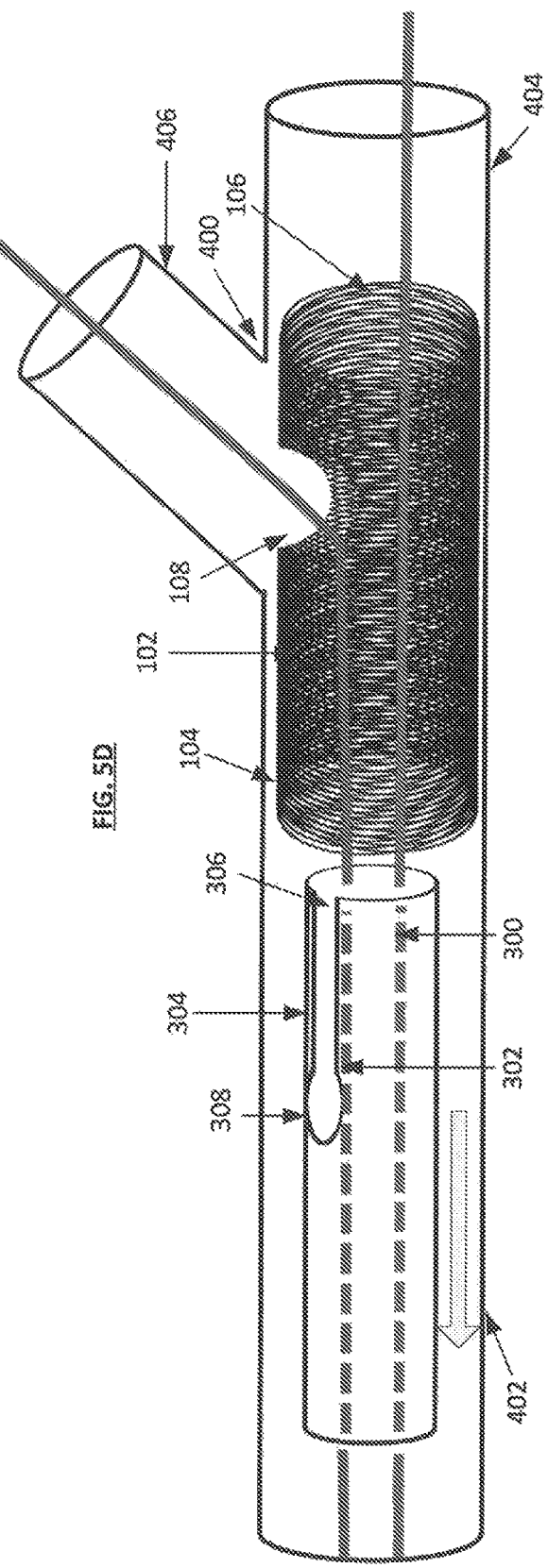

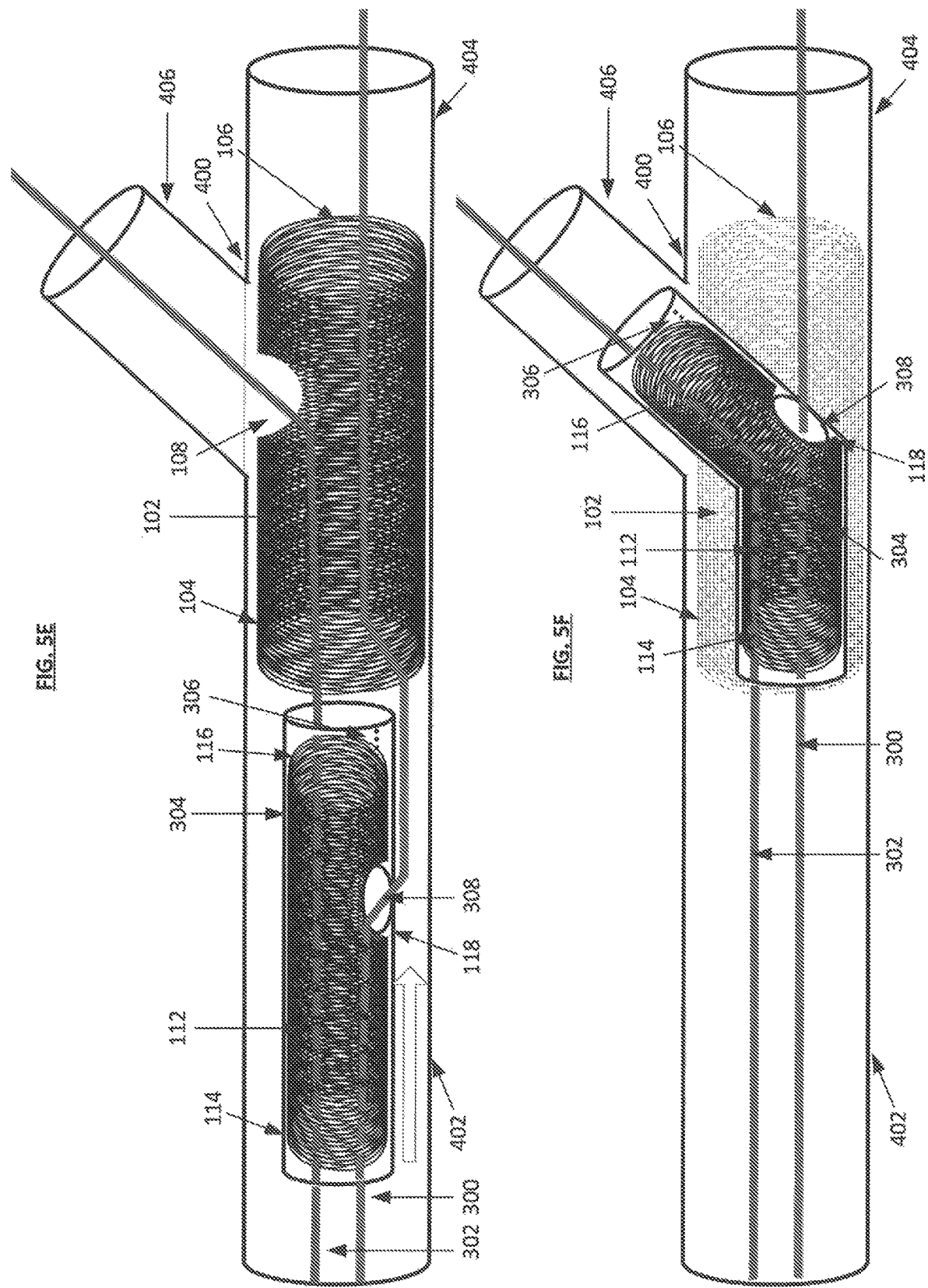

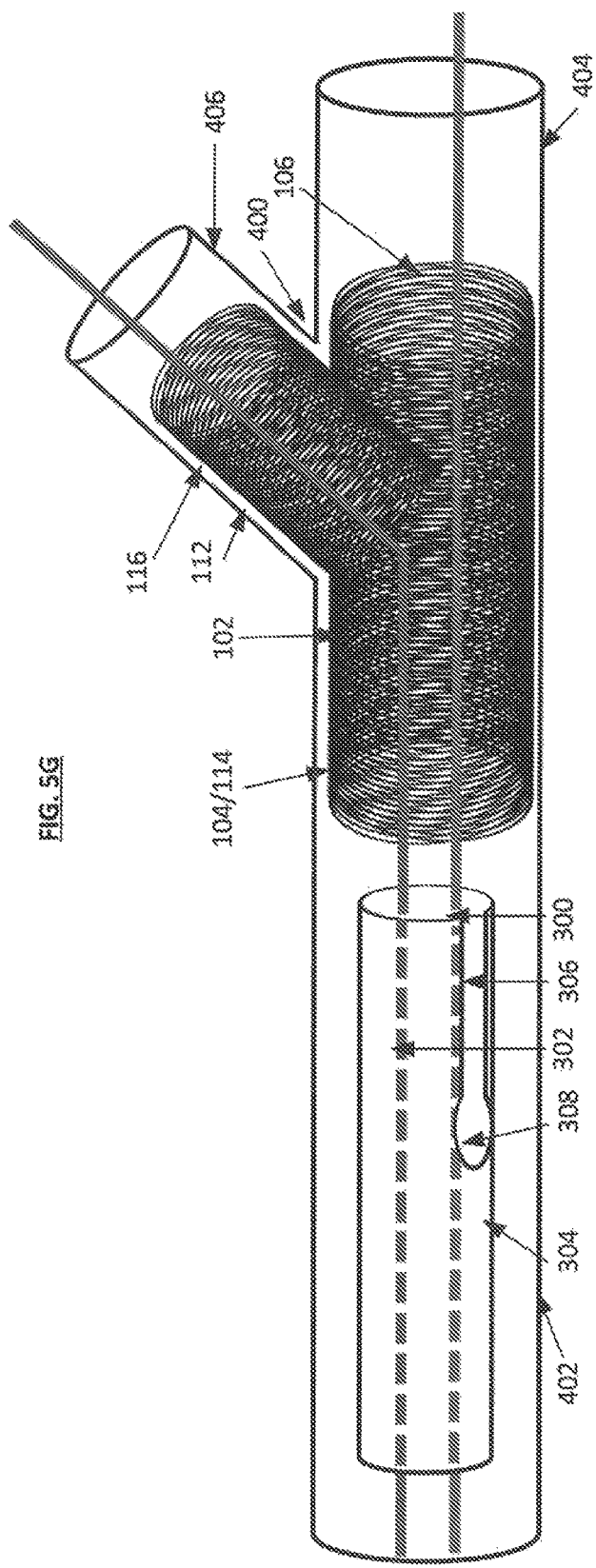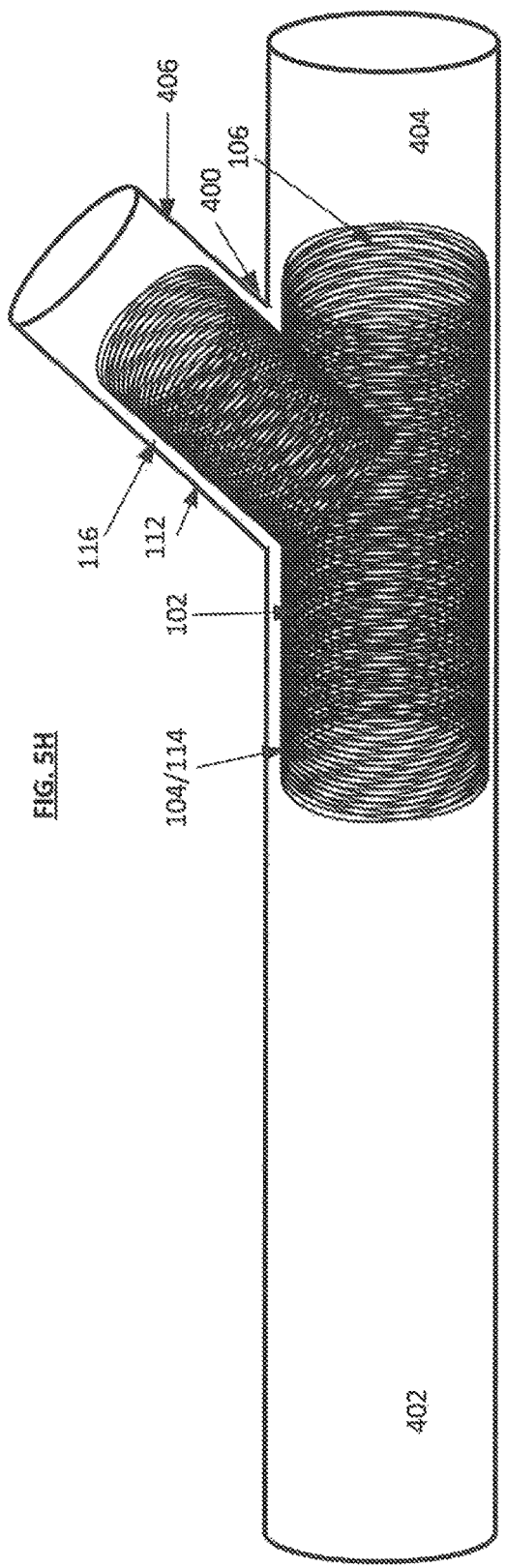

BIFURCATED FLOW DIVERTER SYSTEMS

CROSS-REFERENCE TO RELATED APPLICATION(S)

This application is a national phase application under 35 U.S.C. 371 of International Application No. PCT/US2018/031371, filed May 7, 2018, which claims priority to U.S. Provisional Patent Application Ser. No. 62/502,945, filed May 8, 2017. The entire content of each application is hereby incorporated by reference herein.

BACKGROUND OF THE INVENTION

Wide-necked bifurcation brain aneurysms remain a difficult problem to treat with current technology from both endovascular and open surgical approaches. Currently, flow diversion techniques have provided excellent results in previously untreatable brain aneurysms, but are limited to side wall aneurysms.

SUMMARY OF THE INVENTION

One aspect of the invention provides a flow-diverting system including: a first stent having a proximal end, a distal end and a first sidewall opening; and a second stent having a proximal end, a distal end and a second sidewall opening. The first sidewall opening is of sufficient size for the distal end of the second stent to pass from inside the first stent through the first sidewall opening. The second sidewall opening is of sufficient size for fluid flow from inside the second stent through the second sidewall opening into the first stent.

This aspect of the invention can have a variety of embodiments. The first stent and second stent can each independently have a maximum cross-sectional dimension of about 2.5 mm to about 5 mm. The first stent and the second stent can have a substantially circular cross-sectional shape. The first stent and the second stent can be sufficiently compliant so as to conform to vessels having a substantially oblong cross-section. The first stent and second stent can be adapted and configured for use in intracranial blood vessels.

One or both of the first stent and the second stent can be self-expanding stents. The first stent and the second stent can include one or more materials selected from the group consisting of nickel-titanium alloy, stainless steel, cobalt chromium, platinum, nickel-cobalt chromium alloy, tungsten, tantalum and iridium. Either or both of the first stent and the second stent can be dual-layered stents including an outer self-expanding stent and an inner woven stent.

Either or both of the first stent and the second stent can be dual-layered stents comprising an outer woven stent and an inner self-expanding stent.

Both the first stent and the second stent can be dual-layered stents including an outer self-expanding nitinol stent and an inner woven cobalt-chromium stent having a sidewall opening. The self-expanding nitinol stents can be welded to the exterior of the woven stent.

The first stent and the second stent can be oriented such that: the proximal end of the second stent lies within the proximal end of the first stent; and the distal end of the second stent passes from inside the first stent and through the first sidewall opening such that the distal end of the first stent and the distal end of the second stent form a "Y" or "T" shape. The angle formed by the distal end of the first stent and the distal end of the second stent can be between 0° and 180°. The angle formed by the distal end of the first stent and the distal end of the second stent can be between 0° and 90°.

The first stent and the second stent can each include a central region providing at least about 30% luminal coverage. The central region can be woven.

The flow-diverting system can include a first guide wire and a second guide wire adapted and configured to position and guide the first stent and second stent. The first guide wire can run through: the proximal end of the first stent and second stent; the second sidewall opening of the second stent; and the distal end of the first stent. The second guide wire can run through: the proximal end of the first stent and second stent; the first sidewall opening of the first stent; and through the distal end of the second stent. The flow-diverting system can further include a protective sheath around one or more of the first stent and the second stent. The protective sheath can include a third sidewall opening. Each of the protective sheaths can include one or more perforations distal to the sidewall opening that can be ruptured by proximally pulling the protective sheath in order to deploy the stent.

Another aspect of the invention provides a method of delivering a flow diverting intraluminal device to a blood vessel bifurcation. The flow diverting intraluminal device includes: a first stent, a second stent, a first substantially cylindrical protective sheath, a second substantially cylindrical protective sheath, a first guide wire, and a second guide wire. The first stent has a proximal end, a distal end, and a first sidewall opening. The second stent has a proximal end, a distal end, and a second sidewall opening. The first stent includes a first sidewall opening of sufficient size for the distal end of the second stent to pass from inside the first stent through the first sidewall opening. The second stent includes a second sidewall opening of sufficient size for vascular fluid flow from inside the second stent through the second sidewall opening into the first stent. The first substantially cylindrical protective sheath includes a proximal end, a distal end and a third sidewall opening disposed around the first stent. The second substantially cylindrical protective sheath includes a proximal end, a distal end, and a third sidewall opening disposed around the second stent. The method includes: using a system of one or more catheters to position the first guide wire in a first branch of the blood vessel bifurcation and the second guide wire in a second branch of the blood vessel bifurcation; positioning the first stent at the blood vessel bifurcation using the first guide wire and second guide wire; removing the protective sheath from the first stent such that the first stent expands at the blood vessel bifurcation, and such that the distal end of the first stent is placed within the first branch of the blood vessel bifurcation and the first sidewall opening is aligned with the second branch of the blood vessel bifurcation; passing the distal end of the sheathed second stent through the first sidewall opening of the first stent from inside the first stent such that vascular fluid can flow through the proximal ends of the first stent and second stent, and simultaneously through the second stent, through the second sidewall opening and through the first stent; removing the sheath from the second stent such that the second stent expands at the blood vessel bifurcation; and removing the first guide wire and the second guide wire.

This aspect of the invention can have a variety of embodiments. The protective sheaths can have a series of microperforations running from the third sidewall openings to the distal ends, adapted and configured to split open upon being pulled, allowing for removal of the sheath without disturbing the first and second guide wires.

The one or more catheters can be one or more catheters selected from the group consisting of: distal access catheters, protective sheath catheters, and rapid exchange microcatheters. One or more of the one or more catheters can be over-the-wire catheters. One or more of the one or more catheters can be monorail catheters.

Another aspect of the invention provides a method of fabricating a stent having a proximal end, a distal end and a sidewall opening. The method includes: providing a mandrel defining a central cylinder and a side branch; and winding one or more wires around the mandrel in order to approximate a profile of the central cylinder while creating a sidewall opening approximating a profile of the side branch.

Another aspect of the invention provides an intracranial flow-diverting system comprising: a first stent and a second stent. The first stent includes: a proximal end, a distal end; a woven mesh cylinder between the proximal end and the distal end; and a first sidewall opening through the woven mesh cylinder. The second stent includes: a proximal end; a distal end; a woven mesh cylinder between the proximal end and the distal end; and a second sidewall opening through the woven mesh cylinder. The first sidewall opening is of sufficient size for the distal end of the second stent to pass from inside the first stent through the first sidewall opening. The second sidewall opening is of sufficient size for fluid flow from inside the second stent through the second sidewall opening into the first stent.

This aspect of the invention can have a variety of embodiments. The system can further comprising one or more rapid-exchange balloons. The system can further include one or more catheters adapted and configured to aid in positioning the first and second stents at blood vessel bifurcation.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 1 depicts individual flow diverters as well as the assembled bifurcated flow diverter according to an embodiment of the invention.

FIGS. 2A and 2B depict hybrid dual layer flow diverters having a sidewall opening according to an embodiment of the invention.

FIGS. 4A and 4B depict dual wire access and deployment of flow diverters according to an embodiment of the invention. FIG. 4A depicts the deployment of the first flow diverter and FIG. 4B depicts the deployment of the combined flow diverter system.

FIGS. 5A-5H depict a deployment method of the bifurcated flow diverter system according to an embodiment of the invention.

DEFINITIONS

Figure 3C:
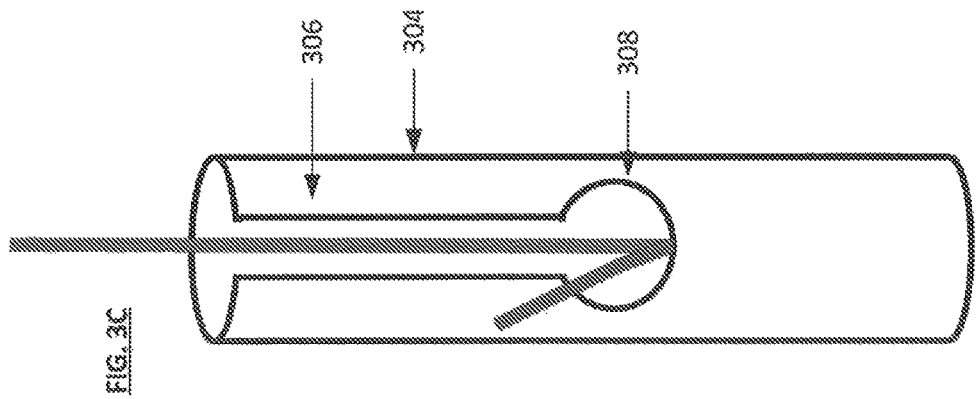
FIGS. 3A-3C depict a protective sheath according to an embodiment of the invention.

The instant invention is most clearly understood with reference to the following definitions:

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

As used herein, the term "aneurysm" refers to an excessive localized enlargement of an artery caused by a weakening of the artery wall.

As used herein, the term "bifurcation" generally refers to a division into two branches, and, more specifically in the context of the invention, a division in a blood vessel into two blood vessels.

The "catheters" as described herein (e.g., sheath catheters, distal access catheters, microcatheters, balloon catheters, and the like) can have a variety of lengths, diameters, quantities of lumens, and other properties. For example, catheters can interact with guide wires through a side-hole exit (e.g., between about 10 cm to 20 cm from a distal tip) colloquially known as a rapid-exchange or monorail architecture. Alternatively, an over-the-wire catheter can include at least one lumen extending through the length of the catheter, through which the catheter can be placed over a guidewire. Rapid-exchange (monorail) and over-the-wire architectures are depicted in FIG. 7-2 of Michael B. Silva & Charlie C. Cheng, "Guidewires, Catheters, and Sheaths", in *Endovascular Surgery* (Wesley S. Moore & Samuel S. Ahn eds., 4th ed. 2011).

As used herein, the term "stent" refers to a small mesh tube that is inserted into the lumen of an anatomic vessel or duct to keep the passageway open. A stent may be one selected from the group of, but not limited to, a coronary stent, a vascular stent, a bilary stent and a ureteral stent. A stent may be made of a number of materials including plastics and metals.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

The present invention provides a system for diverting flow at a vessel bifurcation and methods of deploying said system. In certain embodiments, the system comprises a pair of stents. The system and methods can be used to treat wide-necked bifurcation brain aneurysms in a subject, especially in delicate regions such as the brain.

Bifurcated Flow-Diverting Stents

Referring to FIG. 1, the invention provides a system of bifurcated-Flow-Diverting Stents 100. The system can include two stents having internal lumens: a first stent 102 having a proximal end 104, a distal end 106 and a first sidewall opening 108; and a second stent 112 having a proximal end 114, a distal end 116 and a second sidewall opening 118.

The first sidewall opening 108 can be of sufficient size for the distal end 116 of the second stent 112 to pass from inside the first stent 102 through the first sidewall opening 108. The second sidewall opening 118 can be of sufficient size for fluid (e.g., blood) to flow from inside the second stent 112, through the second sidewall opening 118 and into the first stent 102.

The first sidewall opening 108 can be sized to substantially approximate the outer diameter of the second stent 112 after expansion. In one embodiment, the first sidewall opening 108 is sized to form an interference fit after expansion of the second stent 112. For example, the first sidewall opening 108 can have the same size as the outer diameter of the second stent 112 or can have a cross-sectional dimension less than 10% or less than 5% of the outer diameter of the second stent 112. In one embodiment, the first sidewall opening 108 and/or the second sidewall opening 118 has a substantially elliptical provide adapted and configured to accommodate the passage of a stent 102, 112 at an angle from the central diameter of the vessel 402 within the proximal ends of the stents lie.

When the bifurcated flow-diverting system 100 is assembled, the distal end 116 of the second stent 112 passes through the proximal end 104 of the first stent 102, through the lumen of the first stent 102 and out of the first sidewall opening 108, such that the proximal end 114 of the second stent 112 is disposed within the lumen of the first stent 102 and the distal end 116 extends out of the first sidewall opening 108 in order to form a "Y" shape, as depicted on the right panel of FIG. 1. Alternatively, the assembled system 100 can form a "T" shape. In other embodiments the distal ends 106 and 116 can form any angle θ greater than 0° and less than 180°, greater than 0° and less than 90°, greater than 30° and less than 90°, greater than 45° and less than 90°, and the like. Once assembled, the proximal ends 104, 114 can overlap with one another such that the proximal end 104 of the first stent 102 envelops or substantially envelops the proximal end 114 of the second stent 112. Proximal ends 104, 114 need not be coterminal with each other; rather one proximal end 104, 114 can extend beyond the other proximal end 104, 114 without affecting the operation of the invention.

Referring to FIGS. 2A and 2B, the stents of the invention 102, 112 can be fabricated from one or more segments. In embodiments having two or more segments, the segments can be coupled using press or interference fits (e.g., in which an inner segment is biased to press outward against an outer segment), mechanical fittings (e.g., braiding, wires, fasteners), welding, brazing, soldering, crimping, adhesives, and the like.

Dual-layered stents 200 can include an outer segment 202 and one or more inner segments 204. Although the central segment 202 (relative to proximal and distal ends 104/114, 106/116) is shown as the outer segment, the segments can be sized and/or arranged in any orientation. Likewise, end segments 204 can be a single layer 204 that extends over or through central segment 202 instead of two segments 204. Furthermore, all, some, or none of the segments can have varying degrees of self-expanding and/or flow-occluding properties. For example, end segments 204 can be self-expanding segments that push outward to seat the ends of the stent 200, while the central segment 202 can be a woven stent that defines a confined fluid flow path through the aneurysm. In alternative embodiments, the end segments 204 can be woven stents and the central segment 202 can be self-expanding.

In one embodiment, a central flow-occluding segment 202 covers a majority of the length of the stent 200. For example, a central flow-occluding segment 202 can cover at least about 60%, at least about 70%, at least about 80%, at least about 90%, and the like of the of the total length of the stent. The central flow-occluding segment 202 can be centered with respect to the length of the stent 200 or can be offset.

In one embodiment, an inner woven segment(s) 204 can be inserted into the lumen of an outer self-expanding segment 202. In some embodiments, inner woven segment(s) 204 extend beyond the length of an outer self-expanding central segment 202 such that the inner woven stent(s) 204 define the proximal end 104, 114 and distal end 106, 116.

The stents 102, 112 can be self-expanding stents, such that the stents 102, 112 can be constricted in order to decrease their maximum cross-sectional dimension and upon release of the constriction, return to the un-constricted size without need for any supplementary means of re-expanding. In other embodiments, the stents 102, 112 can be non-self-expanding stents that can be expanded using a device such as angioplasty balloons. The balloons can be rapid exchange balloons and can be either single-lumen or double-lumen balloons.

The stents 102, 112 can each independently have a maximum cross-sectional dimension of about 2.5 mm to about 5 mm. In certain embodiments, the first and second stents 102/112 can have a substantially circular cross-sectional shape in their un-constricted state. The first and second stents 102, 112 can be flexible so that when inserted into the lumen of a vessel, they can conform to the internal shape of the vessel and, for example, take on an oblong cross-sectional shape. In another embodiment, the first and second stents 102, 112 can have a substantially oblong cross-sectional shape.

In certain embodiments, the stents of the invention 102, 112 can be fabricated from one or more materials selected from the group consisting of metals, polymers, and plastics. The stents 102, 112 can include one or more metals and metal alloys selected from the group consisting of shape-memory alloys (e.g., nickel titanium (nitinol)), stainless steel, 316L stainless steel, cobalt-chromium alloy, nickel-cobalt-chromium alloy, tungsten, platinum, iridium and tantalum. Other exemplary shape-memory alloys are described in publications such as Leonardo Lecce & Antonio Concilio, *Shape Memory Alloy Engineering: For Aerospace, Structural and Biomedical Applications* (2014). The stents 102, 112 can also include various non-metallic materials such as plastics such as polyethylene, polyurethane, polytetrafluoroethylene (PTFE), silicone, poly(propylene) (PP), polyethylene terephthalate (PET). The stents 102, 112 can also include one or more shape-memory polymers. Exemplary shape-memory polymers are described in publications such as Jinlian Hu, *Shape Memory Polymers and Textiles* (2007); Jinlian Hu, *Shape Memory Polymers: Fundamentals, Advances and Applications* (2014); and Jinsong Leng & Shanyi Du, *Shape-Memory Polymers and Multifunctional*

*Composites* (2010). In one embodiment, the first stent 102 and second stent 112 are dual-layered stents including an outer self-expanding nitinol segment 202 and an inner woven cobalt-chromium segment 204 having a sidewall opening 108, 118. The outer self-expanding nitinol segments 202 can be welded to the exterior of the inner woven segments 204.

Exemplary dual-layered stents are described in U.S. Patent Application Publication Nos. 2016/0199204 and 2016/0361180.

Central segment 202 can be a woven stent having sufficient occlusiveness to divert flow over time. Without being bound by theory, Applicant believes that coverage (e.g., what percentage of a two-dimensional segment is occupied by the stent) of at least about 30% of the cylindrical surface area by the stent is sufficient to produce clinically effective flow diversion. Additional occlusiveness (e.g., at least about 40% coverage, at least about 50% coverage, at least about 60% coverage, at least about 70% coverage, at least about 80% coverage, at least about 90% coverage, and the like) can be provided.

Figure 3B:
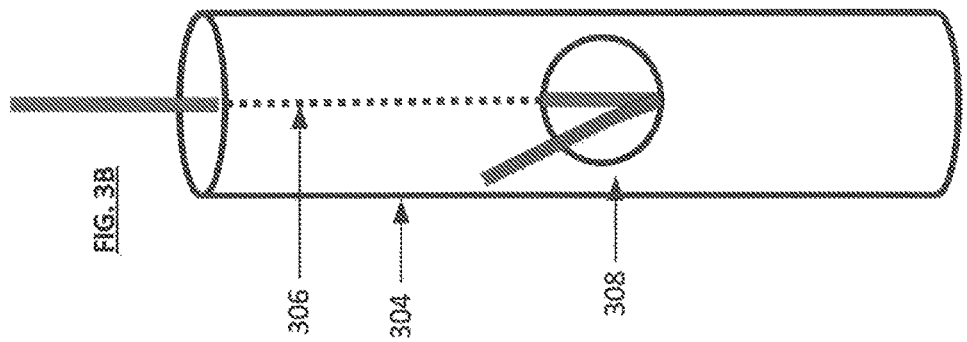
Figure 3A:
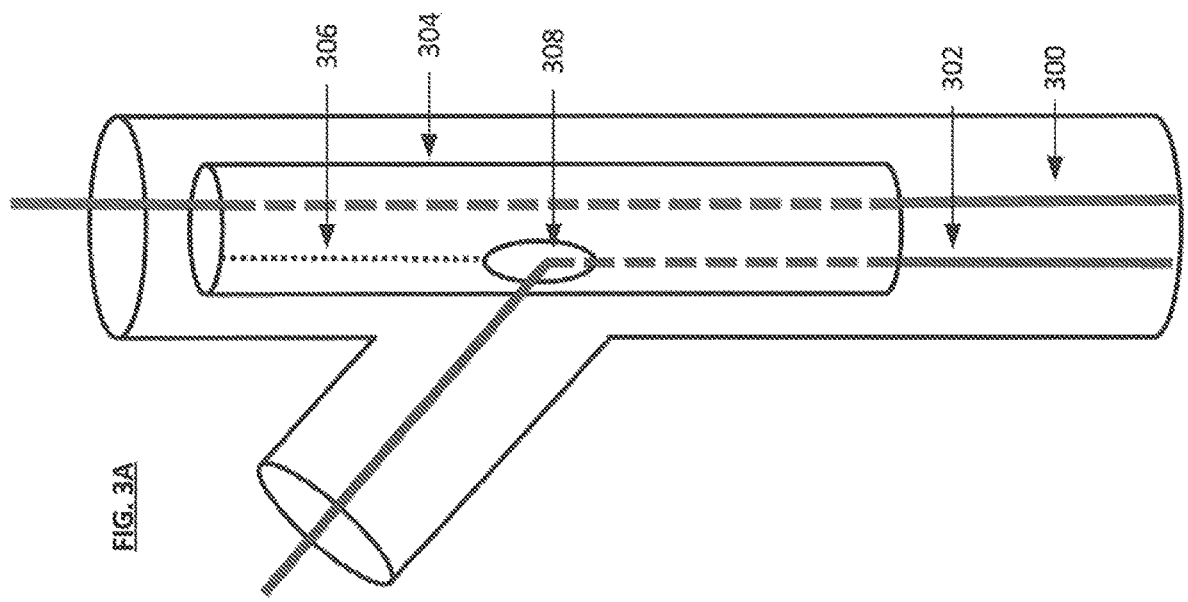

Referring to FIGS. 3A-3C, the system of the invention can further include one or more guide wires 300, 302 and one or more protective sheaths 304.

The system can include a first guide wire 300 and a second guide wire 302 adapted and configured to position and guide the first stent 102 and the second stent 112. Various suitable guide wires are described in publications such as Michael B. Silva & Charlie C. Cheng, "Guidewires, Catheters, and Sheaths", in *Endovascular Surgery* (Wesley S. Moore & Samuel S. Ahn eds., 4th ed. 2011) and are available from a variety of manufacturers such as Boston Scientific Corporation of Marlborough, Mass. The guide wires 300, 302 can be any length necessary to reach from a point of insertion into the blood stream to the location where the first stent 102 and second stent 112 are to be deployed. The wires can be, for instance, about 100 cm to about 500 cm long, more preferably about 150 cm to about 300 cm long. The wires 300, 302 can also have varied rigidities to aid in guiding the wires 300, 302 to a blood vessel bifurcation. For example, the wires 300, 302 can be very stiff along most of the length of the wire and be more flexible towards the distal end.

The one or more protective sheaths 304 can be adapted and configured to contain the first stent 102 and/or the second stent 112. The protective sheaths 304 can have one or more perforations 306 distal to the sidewall opening 308 that can be ruptured by proximally pulling the protective sheath 304 in order to remove the sheath 304 and deploy the stent 102, 112. The protective sheaths 304 can have a third sidewall opening 308 of sufficient size as to allow the first guide wire 300 and/or the second guide wire 302 to pass through. The protective sheaths 304 can be of sufficient strength maintain the stents 102, 112 in a compressed state, but capable of rupture through proximal withdrawal.

The first stent 102 and the second stent 112 can be contained within the one or more protective sheaths 304, such that while disposed within the protective sheaths 304, the stents 102, 112 are diametrically constricted. The stents 102, 112 can be self-expanding stents such that when the perforation 306 is ruptured and the sheaths 304 are removed, the stents 102, 112 expand outward.

Methods of Deploying Bifurcated Flow-Diverting Systems

Figure 4A:
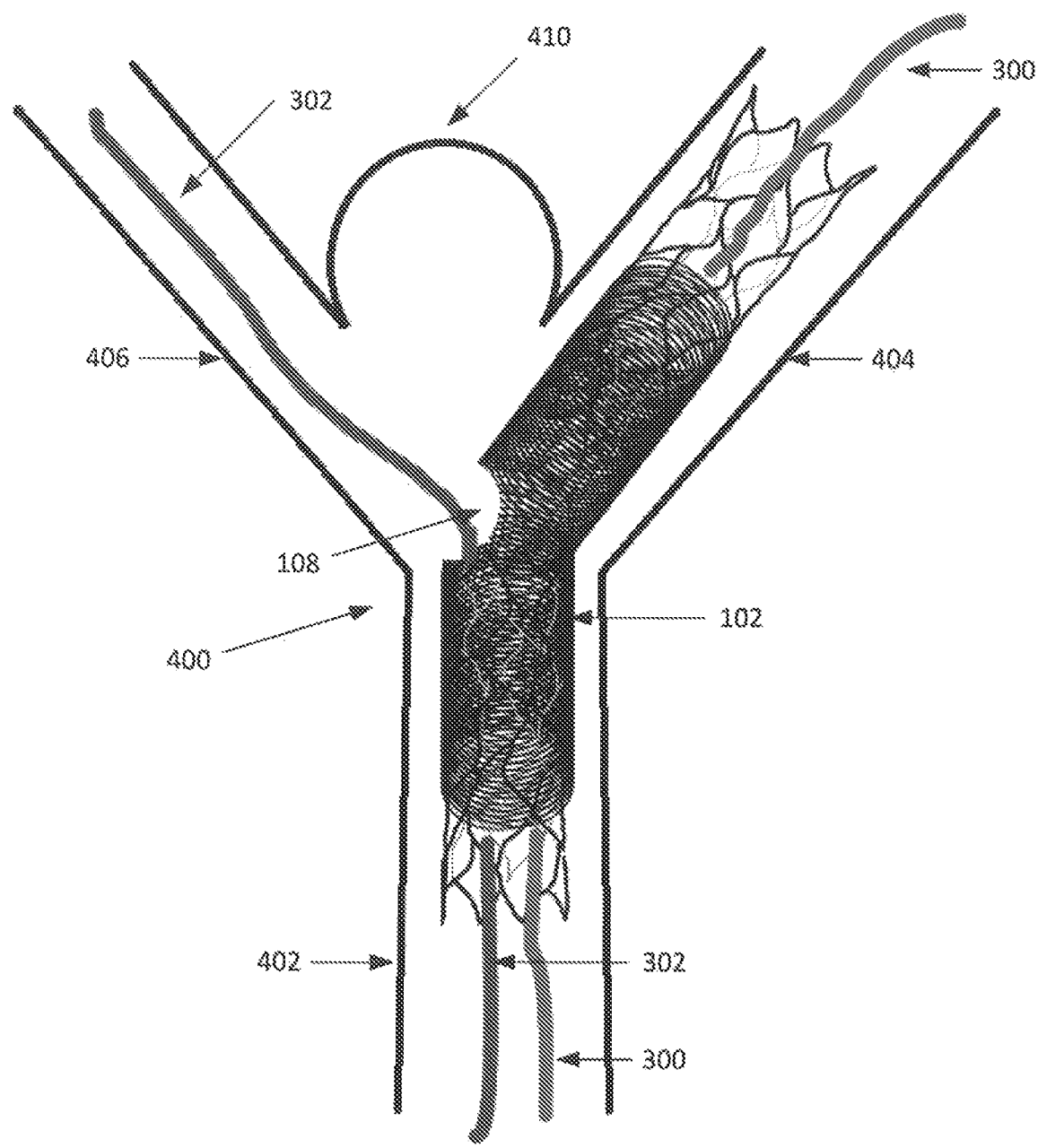

Referring to FIGS. 4A and 4B, the invention further provides a method of delivering the flow-diverting system 100 to a blood vessel bifurcation such that the first stent 102 and the second stent 112 extend down different branches 404, 406 of the blood vessel bifurcation 400.

The flow-diverting system 100 can be deployed at a blood vessel bifurcation 400 where a single vessel 402 branches into two vessels 404, 406. The flow-diverting system 100 can be used to divert blood flow away from an aneurysm 410 located at a blood vessel bifurcation 400.

FIGS. 5A-5H depict an exemplary method for deploying the system 100.

Referring now to FIG. 5A, a first guide wire 300 is advanced through a bifurcated blood vessel 402 and into a first blood vessel branch 404 of the blood vessel bifurcation 400. A second guide wire 302 is advanced through a bifurcated blood vessel 402 and into a second blood vessel branch 406 of the blood vessel bifurcation 400. The guide wires 300, 302 can enter the patient's blood vessel through an access point (e.g., at the patient's femoral artery). Other suitable arterial access sites are described in George Andros, "Arterial Access" in *Endovascular Surgery* (Wesley S. Moore & Samuel S. Ahn eds., 4th ed. 2011). Proper positioning of the guide wires 300, 302 can be verified using various imaging modalities such fluoroscopy.

In one embodiment, a distal access guide catheter is used to approach the aneurysm. The guide wires 300, 302 can be indwelling within the distal access guide catheter during advancement or can be passed through the lumen of the distal access guide catheter after the guide catheter approaches the aneurysm.

Alternatively, a guiding sheath (e.g., the FLEXOR® SHUTTLE® Guiding Sheath marketed by Cook Medical of Bloomington, Ind., the AXS INFINITY LS™ marketed by Stryker Neurovascular of Fremont, Calif., or the NEURON™ System marketed by Penumbra Inc. of Alameda, Calif.) could be positioned such that a first distal support catheter (e.g., the NAVIEN™ 072 catheter marketed by Medtronic of Fridley, Minn. or the CAT™ 6 marketed by Stryker Neurovascular of Fremont, Calif.) could be advanced through the guiding sheath. Through the first distal support catheter, a second smaller distal support catheter (e.g., the PHENOM™ Plus 0445 catheter marketed by Medtronic of Fridley, Minn.) could be placed, guiding the guide wires 300, 302 to the aneurysm. The catheter stent system 100 can be pushed through one of the distal access catheters positioned close to the neck of an aneurysm.

In another embodiment, the wires 300, 302 can be positioned using a monorail (Rx) catheter. The use of a monorail system can allow for a greater capacity for pushing the catheter when compared to over-the-wire catheters and may allow for easier positioning in the middle cerebral artery or other brain bifurcations. Additionally, a monorail catheter allows for the use of shorter guide wires 300, 302 (for example, 150 cm).

Referring now to FIG. 5B, the first stent 102 within a first protective sheath 304 is placed over the guide wires (e.g., outside the patient's body at the access point) such that the first guide wire 300 runs through the proximal end 104 of the stent, through the protective sheath 304 and through the distal end 106 of the stent, and the second guide wire 302 runs through the proximal end 104 of the stent, through a portion of the protective sheath 304 and through both the first sidewall opening 108 and the third sidewall opening 308.

Referring now to FIG. 5C, the sheathed first stent 102 is advanced over the guide wires 300, 302 to the blood vessel bifurcation 400. The sheathed first stent 102 can be pushed along a path defined by the guide wires 300, 302 by an instrument (e.g., a pusher guide wire, a delivery catheter, and the like) adapted to ride over one or both guide wires 300, 302. One exemplary instrument is described in U.S. Pat. No. 5,102,403. Proper positioning of the first stent 102 can be verified using various imaging modalities such fluoroscopy.

Referring now to FIG. 5D, the first protective sheath 304 is removed, and allowing the first stent 102 to expand such that the distal end 106 of the first stent 102 is placed within the first branch 404 of the blood vessel bifurcation and the first sidewall opening 108 is aligned with the second branch 406 of the blood vessel bifurcation. In one embodiment, the protective sheath 304 is pulled proximally while the underlying first stent 102 is held in place (e.g., by the instrument that advanced the compressed first stent 102 into the desired position). The first protective sheath 304 can be pulled by a string or other instrument. As the first protective sheath 304 is pulled, the perforated region contacts second guide wire 302 and ruptures, allowing the first stent 302 to expand.

Referring now to FIG. 5E, the second stent 112 within a second protective sheath 304 is positioned (e.g., outside the patient's body at the access point) such that the first guide wire 400 runs through the proximal end 114 of the second stent 112, through a portion of the protective sheath 304 and through both the second sidewall opening 118 and the third sidewall opening 308, and the second guide wire 302 runs through the proximal end 114 of the second stent 112, through the protective sheath 304 and through the distal end 116 of the second stent 112.

Referring now to FIG. 5F, the sheathed second stent 112 is advanced to the blood vessel bifurcation 400, feeding it through the expanded first stent 102, such that the distal end 116 of the second stent 112 passes through the first sidewall opening 108 from inside the first stent 102. The sheathed second stent 112 can be advanced using the same techniques and devices described in the context of the first stent 102.

Referring now to FIG. 5G, the second protective sheath 304 is removed, allowing the second stent 112 to expand such that the distal end 116 of the second stent 112 is placed within the second branch 406 of the blood vessel bifurcation and the second sidewall opening 118 is aligned such that fluid can flow through the proximal ends 104, 114 of the first stent 102 and second stent 112 and then through both (i) the second sidewall opening 118 and through the distal end 106 of the first stent 102 and (ii) the first sidewall opening 108 and the through the distal end 116 of the second stent 112.

Referring now to FIG. 5H, the first guide wire 300 and the second guide wire 302 are withdrawn proximally.

Placement of the first stent 102 and second stent 112 can be aided by the use of one or more catheters.

In certain embodiments, the perforations 306 on the protective sheath 304 are micro-perforations which split open as the sheaths are pulled proximally, without disturbing the guide wires 300, 302. The micro-perforations can be a series of holes with an average diameter of about 45 μm to about 400 μm. In order to rupture the perforations 306, the sheath should only require about 5 gram-force to about 15 gram-force of pulling force. The perforations 306 should be strong enough so that the sheath does not rupture under the force needed to contain the unexpanded stents but should not be so strong that the force required to split the perforations 306 would be enough to cause damage to the surrounding vessels.

The methods of the invention can be used to treat wide-necked bifurcation brain aneurysms in a subject, especially in delicate regions such as the brain. Although the methods and devices described herein are particularly useful in the delicate and challenging regions of the brain, embodiments of the invention can be sized and/or adapted for treatment of other aneurysms in other anatomic locations.

Methods of Fabricating Bifurcated Flow-Diverting Systems

The invention also provides methods of making the stents of the invention. In one embodiment, the method comprises providing a mandrel defining a central cylinder and a side branch and winding one or more wires around the mandrel in order to approximate a profile of the central cylinder while creating sidewall opening approximating a profile of the side branch. Such a method will provide the desired geometry while minimizing burrs or other sharp edges that may occur the sidewall openings are cut into prefabricated stents.

Kits

The invention further provides kits comprising the elements disclosed elsewhere herein.

In one embodiment, the invention provides a kit including a first stent 102 and a second stent 112 as described herein. The stents 102, 112 can be sheathed.

The kit can further include lengths of guide wire, including a first guide wire 300 and a second guide wire 302. In order to aid in distinguishing the guide wires, the different lengths of wire can have different colors or markings. The stents could also be colored or labeled for verification that the guidewires pass through the appropriate openings.

The kit can further include one or more instruments for advancing the sheathed stents and withdrawing the sheaths.

A set of instructional materials can also be provided in the kit. The instructional materials can contain written, pictorial, and/or video directions on using the materials of the kit, including the methods of the invention. One or more training phantoms having a branched path can also be included.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A flow-diverting system comprising:
 a first stent having a proximal end, a distal end and a first sidewall opening;
 a second stent having a proximal end, a distal end and a second sidewall opening;
 a first guide wire; and
 a second guide wire;
 wherein:
  the first sidewall opening is of sufficient size for the distal end of the second stent to pass from inside the first stent through the first sidewall opening;
  the second sidewall opening is of sufficient size for fluid flow from inside the second stent through the second sidewall opening into the first stent;
  the first guide wire runs through:
   the proximal end of the first stent and the second stent;
   the second sidewall opening of the second stent; and
   the distal end of the first stent; and
  the second guide wire runs through:

the proximal end of the first stent and the second stent;

the first sidewall opening of the first stent; and through the distal end of the second stent; and both the first stent and the second stent are dual-layered stents comprising:

an outer self-expanding nitinol stent; and an inner woven cobalt-chromium stent having a sidewall opening;

wherein the self-expanding nitinol stent is welded to the exterior of the corresponding woven stent.

2. The flow-diverting system of claim 1, wherein the first stent and second stent each independently have a maximum cross-sectional dimension of about 2.5 mm to about 5 mm.

3. The flow-diverting system of claim 1, wherein the first stent and the second stent have a substantially circular cross-sectional shape.

4. The flow-diverting system of claim 3, wherein the first stent and the second stent are sufficiently compliant so as to conform to vessels having a substantially oblong cross-section.

5. The flow-diverting system of claim 1, wherein the first stent and second stent are adapted and configured for use in intracranial blood vessels.

6. The flow-diverting system of claim 1, wherein one or both of the first stent and the second stent are self-expanding stents.

7. The flow-diverting system of claim 1, wherein the first stent and the second stent can be oriented such that:

the proximal end of the second stent lies within the proximal end of the first stent; and the distal end of the second stent passes from inside the first stent and through the first sidewall opening such that the distal end of the first stent and the distal end of the second stent form a "Y" or "T" shape.

8. The flow-diverting system of claim 7, wherein the angle formed by the distal end of the first stent and the distal end of the second stent is selected from the group consisting of: between 0° and 180° and between 0° and 90°.

9. The flow-diverting system of claim 1, wherein the first stent and the second stent each include a central region providing at least about 30% luminal coverage.

10. The flow-diverting system of claim 9, wherein the central region is woven.

11. The flow-diverting system of claim 1, further comprising a protective sheath around one or more of the first stent and the second stent, the protective sheath having a third sidewall opening.

12. The method of claim 11, wherein the protective sheath includes one or more perforations distal to the sidewall opening that can be ruptured by proximally pulling the protective sheath in order to deploy the stent.

13. A method of delivering a flow diverting intraluminal device to a blood vessel bifurcation, wherein the flow diverting intraluminal device comprises:

a first stent having a proximal end, a distal end, and a first sidewall opening; and a second stent having a proximal end, a distal end, and a second sidewall opening;

wherein:

the first stent includes a first sidewall opening of sufficient size for the distal end of the second stent to pass from inside the first stent through the first sidewall opening;

the second stent includes a second sidewall opening of sufficient size for vascular fluid flow from inside the second stent through the second sidewall opening into the first stent; and both the first stent and the second stent are dual-layered stents comprise:

an outer self-expanding nitinol stent; and an inner woven cobalt-chromium stent having a sidewall opening;

wherein the self-expanding nitinol stent is welded to the exterior of the corresponding woven stent;

a first substantially cylindrical protective sheath having a proximal end, a distal end and a third sidewall opening disposed around the first stent; and a second substantially cylindrical protective sheath having a proximal end, a distal end and a third sidewall opening disposed around the second stent;

a first guide wire; and a second guide wire;

the method comprising:

using a system of one or more catheters to position the first guide wire in a first branch of the blood vessel bifurcation and the second guide wire in a second branch of the blood vessel bifurcation;

positioning the first stent at the blood vessel bifurcation using the first guide wire and second guide wire;

removing the protective sheath from the first stent such that the first stent expands at the blood vessel bifurcation, and such that the distal end of the first stent is placed within the first branch of the blood vessel bifurcation and the first sidewall opening is aligned with the second branch of the blood vessel bifurcation;

passing the distal end of the sheathed second stent through the first sidewall opening of the first stent from inside the first stent such that vascular fluid can flow through the proximal ends of the first stent and second stent, and simultaneously through the second stent, through the second sidewall opening and through the first stent;

removing the sheath from the second stent such that the second stent expands at the blood vessel bifurcation; and removing the first guide wire and the second guide wire.

14. The method of claim 13, wherein the protective sheaths have a series of micro-perforations running from the third sidewall openings to the distal ends, adapted and configured to split open upon being pulled, allowing for removal of the sheath without disturbing the first and second guide wires.

15. An intracranial flow-diverting system comprising:

a first stent comprising:

a proximal end, a distal end;

a woven mesh cylinder between the proximal end and the distal end; and a first sidewall opening through the woven mesh cylinder;

a second stent comprising:

a proximal end;

a distal end;

a woven mesh cylinder between the proximal end and the distal end; and a second sidewall opening through the woven mesh cylinder;

a first guide wire; and a second guide wire;

wherein:

the first sidewall opening is of sufficient size for the distal end of the second stent to pass from inside the first stent through the first sidewall opening; and the second sidewall opening is of sufficient size for fluid flow from inside the second stent through the second sidewall opening into the first stent;

the first guide wire runs through:
- the proximal end of the first stent and the second stent;
- the second sidewall opening of the second stent; and
- the distal end of the first stent; and the second guide wire runs through:
- the proximal end of the first stent and the second stent;
- the first sidewall opening of the first stent; and
through the distal end of the second stent; and
- both the first stent and the second stent are dual-layered stents comprise:
- an outer self-expanding nitinol stent; and
- an inner woven cobalt-chromium stent having a sidewall opening;
- wherein the self-expanding nitinol stent is welded to the exterior of the corresponding woven stent.

16. The system of claim 15, further comprising one or more rapid-exchange balloons.

* * * * *